(12) United States Patent
Junior et al.

(10) Patent No.: US 10,695,286 B2
(45) Date of Patent: Jun. 30, 2020

(54) DERMOCOSMETIC COMPOSITION, PRODUCTION PROCESS OF THE TOPICAL COMPOSITION, METHOD FOR STRENGTHENING FRAGILE NAILS AND USE OF THE COMPOSITION

(71) Applicant: BIOLAB SANUS FARMACÊUTICA LTDA., Taboão da Serra (BR)

(72) Inventors: Dante Alário Junior, São Paulo (BR); José Luiz Aiello Ritto, Jundiai (BR)

(73) Assignee: BIOLAB SANUS FARMACÊUTICA LTDA, Taboão da Serra, SP (BR)

( * ) Notice: Subject to any disclaimer, the term of this patent is extended or adjusted under 35 U.S.C. 154(b) by 0 days.

(21) Appl. No.: 15/782,015

(22) PCT Filed: Apr. 11, 2017

(86) PCT No.: PCT/BR2017/050085
§ 371 (c)(1),
(2) Date: Jun. 6, 2018

(87) PCT Pub. No.: WO2017/177295
PCT Pub. Date: Oct. 19, 2017

(65) Prior Publication Data
US 2018/0360734 A1 Dec. 20, 2018

Related U.S. Application Data

(60) Provisional application No. 62/320,844, filed on Apr. 11, 2016.

(51) Int. Cl.
| | | |
|---|---|---|
| *A61K 8/00* | (2006.01) | |
| *A61K 8/9794* | (2017.01) | |
| *A61K 36/899* | (2006.01) | |
| *A61Q 3/00* | (2006.01) | |
| *A61K 8/73* | (2006.01) | |
| *A61K 9/08* | (2006.01) | |
| *A61K 47/10* | (2017.01) | |
| *A61K 47/36* | (2006.01) | |

(52) U.S. Cl.
CPC ............. *A61K 8/9794* (2017.08); *A61K 8/73* (2013.01); *A61K 9/08* (2013.01); *A61K 36/899* (2013.01); *A61K 47/10* (2013.01); *A61K 47/36* (2013.01); *A61Q 3/00* (2013.01)

(58) Field of Classification Search
None
See application file for complete search history.

(56) References Cited

U.S. PATENT DOCUMENTS

| 2007/0122492 A1* | 5/2007 | Behr ..................... A61Q 17/04 424/725 |
| 2011/0183016 A1* | 7/2011 | Mailland ............... A61K 8/342 424/750 |
| 2016/0303033 A1 | 10/2016 | Beyer et al. |

FOREIGN PATENT DOCUMENTS

| FR | 2 442 632 A1 | 6/1980 |
| JP | 2013-060410 A | 4/2013 |

OTHER PUBLICATIONS

Database GNPD [Online] MINTEL; Apr. 2010 (Apr. 2010), "Woori Gokmul Fermented Nutri Eye Cream", XP002773577, Database accession No. 1300782, the whole document.
Database GNPD [Online] MINTEL; Dec. 2005 (Dec. 2005), "Dermal Repair Facial Cream", XP002773579, Database accession No. 10244336, the whole document.
Database GNPD [Online] MINTEL; Dec. 2012 (Dec. 2012), "Overnight Repair Mask", XP002773578, Database accession No. 1963186, the whole document.
International Search Report and Written Opinion dated Sep. 29, 2017 issued in International Application No. PCT/BR2017/050085.
Schmidt, K.H., "Comparing the mechanism of action of different active ingredience in treatment of brittle nails", H&G Zeitschrift Fur Hautkrankheiten, Grosse, DE, vol. 68, No. 8, Jan. 1, 1993 (Jan. 1, 1993), pp. 517-520, XP009195432, ISSN: 0301-0481, the whole document.

\* cited by examiner

*Primary Examiner* — Susan T Tran
(74) *Attorney, Agent, or Firm* — Arent Fox, LLP

(57) ABSTRACT

The present invention relates to a dermocosmetic composition comprising natural substances for topical use, to improve the appearance, protection and strengthening of nails as well as assisting in the recovery of nail disorders. Additionally, the present invention also relates to a process for preparing said composition, a method for strengthening of fragile nails, and the use of this composition in the preparation of a topical composition for the treatment of nail disorders.

27 Claims, 1 Drawing Sheet

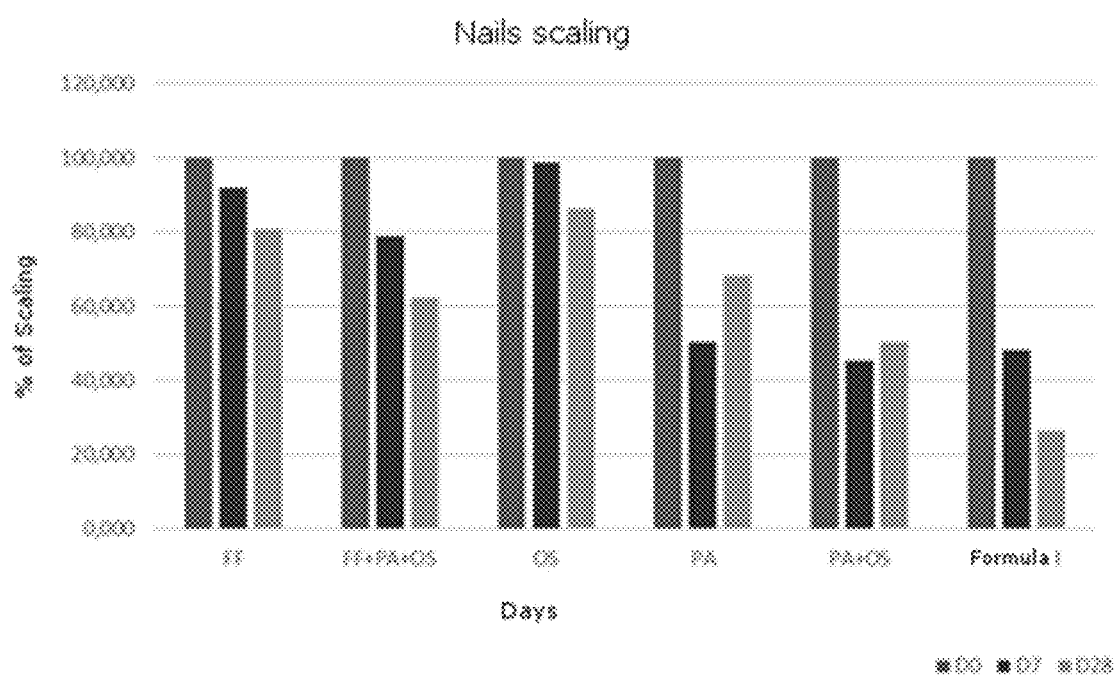

DERMOCOSMETIC COMPOSITION, PRODUCTION PROCESS OF THE TOPICAL COMPOSITION, METHOD FOR STRENGTHENING FRAGILE NAILS AND USE OF THE COMPOSITION

CROSS-REFERENCE TO RELATED APPLICATIONS

This application is a National Stage entry of International Application No.: PCT/BR2017/050085, filed Apr. 11, 2017, which claims priority to U.S. Provisional Application No. 62/320,844, filed Apr. 11, 2016. The disclosures of the priority applications are hereby incorporated in their entirety by reference.

FIELD OF THE INVENTION

The present invention relates to a topical dermocosmetic composition comprising at least one extract of the genus *Panicum*, at least one extract of the genus *Oryza*, and at least one film forming agent and its topical use to improve the appearance of the nails. Additionally, the present invention relates to the use of said composition to treat disorders/alterations of the nails such as reduced resistance, onychoschizia, onychorexis and nail fragility.

Fundamentals of the Invention

As part of the integumentary system, the nail apparatus is of great importance, both functional and aesthetic. Nails are keratinized blades that cover the distal portion of the phalanges.

In addition to the aesthetic function that the nails exercise in our body, especially in women, they act in the protection against trauma to the distal phalanx and adjacent soft tissues and also assist in the performance of all precision manual activities performed in daily life. The functions of the nails can be summarized as: defense, holding/clamping, protection, tactile and aesthetic. When combined with a physical examination, the aspect of the nails can also be indicative of the health of the individual.

The nails are basically composed of protein, especially keratin, as well as water, minerals and lipids. The main component responsible for resistance of the nail is keratin. Although the nails should be sturdy, they must also be flexible, bright, transparent, smooth and without irregularities in the nail plate.

Repeated assaults, such as the use of nail polish, solvents and detergents, along with exaggerated manipulation of the nails, poor diet, injury, fungi and infections, and even excessive contact with water, are some of the important factors that influence appearance, strength and nail growth, often promoting significant changes in the appearance of the nail plate.

Weakening of the nails is a universal complaint. Aspects such as cracked or split nails, dry and brittle nails, peeling of the nail tip and poor growth are characteristic of fragile nail syndrome (FUS).

According to epidemiological data, it is estimated that FUS affects approximately 20%-30% of the general population, and may reach 40%, considering only the female population. The main nail disorders/nail changes that can be observed in patients suffering from FUS are: onychoschizia and onychorexis, followed by other alterations such as distal horizontal fissure of the nail plate, longitudinal grooves, depressions and changes in nail thickness.

More specifically, in onychoschizia is observed a lamellar peeling of the free edge of the nail, i.e., fragile nails with peeling. In onychorexis is observed a thinning of the nail plate with the presence of cracks or fragmentation that may reach the free edge with the possibility of breakage.

Several treatments are indicated for strengthening of the nails. The treatments range from a simple change of habits, increased consumption of foods rich in vitamins (e.g. biotin—vitamin $B_7$), proteins and minerals, improved hygiene habits such as washing of the hands, having clean and trimmed nails, use of moisturizers and acetone-free nail polish remover, the use of gloves when performing tasks with detergents and abrasives, to the use of a strengthening agent, among others.

According to medical practice, the main treatment for brittle nails is often made with biotin-based nutritional supplementation (vitamin $B_7$).

Biotin is an essential, water soluble vitamin, also known as Vitamin $B_7$, Vitamin H or coenzyme R, which functions as a coenzyme. Biotin has action in the metabolism of proteins and carbohydrates and acts directly in the formation of skin and nails.

An example of treatment with biotin is found in the document U.S. Pat. No. 5,155,168. Said document discloses a formulation for topical use comprising biotin associated with various chemical substances to treat nail disorders. More specifically, said document is a method to treat nail disorders through the use of a topical composition comprising a quantity of biotin and a pharmaceutically acceptable salt thereof.

Although biotin presents no toxic risks, or is associated with unwanted side effects, its constant use can trigger allergic processes in users.

When looking for product options focused on nail strengthening, the cosmetics industry developed product lines of bases and nail polishes containing "nail strengthening complexes". The components of these complexes vary according to industry and range from the association of vitamins and oils to the use of keratin alone or keratin associated with calcium.

Keratin is a protein synthesized naturally by many animals for the formation of various body structures. Keratin synthesis occurs in differentiated cells, called keratinocytes, from epithelial tissue (skin) and invaginations from the epidermis to the dermis (such as the hair and nails) of terrestrial animals. Keratin is considered a structural protein, since its three-dimensional structure gives it special characteristics, such as microfilaments with resistance, elasticity and impermeability to water. In mammals, including humans, keratin is present in the skin and hair and is part of the formation of the nails.

In order to find alternatives to develop products with greater effectiveness and fewer unwanted user side effects, researchers have been working on new formulations, as it is possible to verify in the prior art, these formulations being for oral or topical use containing in their composition isolated plant extracts and/or being associated with vitamins and specific film forming agents seeking an improvement in nail quality.

Document WO9505146 discloses the use of an oral composition for the treatment of hair loss and fragile/weak nails. Among the various components present in the formulation, are some plant extracts, such as dried sesame extract and seaweed extract, associated with vitamins and other compounds.

In the search for natural active ingredients, the teachings described in FR 2 610 523 disclose a biogenic extract, obtained by means of *Equisetum arvense*, associated with an appropriate excipient, in a preparation for therapeutic application in connective tissue injuries to strengthen the nails.

Document WO2002/007683 discloses a composition comprising at least one antimycotic agent and at least one film forming agent—film derived from chitosan—preferably with the use of hydroxy propyl methyl chitosan. The document also cites that the invention is directed to the use of a water-soluble film forming agent as a differential additive in a nail varnish.

Document U.S. Pat. No. 5,910,383 discloses the use of a colloidal silicic acid in a nail varnish composition. However, because it is an acid, it is not possible to rule out the fact that some people have intolerance to this type of compound.

Therefore, in spite of existing alternatives in the technique for the treatment of nails, the efficacy results achieved are not widely satisfactory, and it is clear that there is still a need for improvement and the search for new active ingredients and excipients for the production of a dermocosmetic composition that solves the problems related to the appearance of the nails, especially to their fragility, and which acts in the treatment of nail disorders/changes, which overcomes the aesthetic and dermatological disadvantages which still exist.

SUMMARY OF THE INVENTION

The present invention relates to a topical dermocosmetic composition comprising at least one extract of the genus *Paincum*, at least one extract of the genus *Oryza*, indicated as a fragile nail enhancer, having the effect of restructuring, hydrating, hardening and strengthening the nail and, consequently, improving its quality and appearance, and favoring the recovery of nail disorders. Further aspects of the present invention consist of a method for preparing said composition, a method for strengthening fragile nails and the use of the present composition in the preparation of a dermocosmetic agent for treating nail disorders.

BRIEF DESCRIPTION OF THE DRAWINGS

FIG. 1 refers to comparative data in percentage of groups when evaluating clinical efficacy for nail desquamation. The graph shows the percentage of peeling at the start of the study (before use of the investigated product) (D0) and after 07 (D7) and 28 (D28) days of study.

DESCRIPTION OF THE INVENTION

The present invention relates to a dermocosmetic composition for topical use based on plant extracts and a film forming agent. In general, said composition acts as a nail strengthener, improving its quality and appearance and favors the recovery of nail disorders.

More specifically, the composition of the present invention has a dermocosmetic function and comprises as its active ingredient a combination of at least two plant extracts of plants selected from the genera *Panicum* and *Oryza*.

Additionally, the present composition comprises at least one film forming agent and pharmaceutically acceptable excipients.

Optionally, the present composition may further comprise at least one keratin and/or biotin.

More particularly, said dermocosmetic topical composition may be in the form of a gel, nail polish, lotion, solution or suspension. Such forms facilitate the application of the dermocosmetic composition in the nail and improving the penetration of the active ingredients in the nail plate due to the formation of a film on the nail.

The present composition is especially suitable for fragile nail syndrome, acting as a nail strengthener, and having the effect of restructuring, hydration, hardening and strengthening of nails.

Another aspect of the present invention comprises a process for preparing said composition.

Another aspect of the present invention comprises a method for strengthening of fragile nails comprising topical application of said composition.

A final aspect of the present invention comprises the use of this composition in the preparation of a dermocosmetic to treat nail disorders, particularly those related to fragile nail syndrome (onychoschizia, onychorexis, etc.) resulting from nail diseases or exogenous causes as, for example, chemical agents or trauma.

According to the present invention, the composition comprises at least one *Panicum* extract, selected from any species of the genus consisting of: *Panicum amarum, Panicum ambiguum, Panicum anabaptistum, Panicum anceps, Panicum antidotale, Panicum aquaticum, Panicum arechavaletae, Panicum bartowense, Panicum bergii, Panicum bisulcatum, Panicum brachyanthum, Panicum brevifolium, Panicum bulbosum, Panicum campestre, Panicum capillare, Panicum capillarioides, Panicum coloratum, Panicum curviflorum, Panicum decolorans, Panicum decompositum, Panicum deustum, Panicum dichotomiflorum, Panicum dregeanum, Panicum effusum, Panicum flavescens, Panicum fluviicola, Panicum fulgidum, Panicum gattingeri, Panicum ghiesbreghtii, Panicum glabripes, Panicum gracilicaule, Panicum grumosum, Panicum gymnocarpon, Panicum hallii, Panicum havardii, Panicum hemitomon, Panicum hillmanii, Panicum hirstii, Panicum hirsutum, Panicum hirticaule, Panicum hochstetteri, Panicum kalaharense, Panicum lanipes, Panicum larcomianum, Panicum laxum, Panicum massaiense, Panicum miliaceum, Panicum milioides, Panicum millegrana, Panicum mindanaense, Panicum missionum, Panicum monticola, Panicum natalense, Panicum nephelophilum, Panicum niihauense, Panicum notatum, Panicum numidianum, Panicum obtusum, Panicum olyroides, Panicum paludosum, Panicum pernambucense, Panicum philadelphicum, Panicum phragmitoides, Panicum pilosum, Panicum plenum, Panicum plicatum, Panicum poaeoides, Panicum polygonatum, Panicum prionitis, Panicum psilopodium, Panicum quadriglume, Panicum queenslandicum, Panicum racemosum, Panicum radicans, Panicum repandum, Panicum repens, Panicum reverchonii, Panicum rigidulum, Panicum schinzii, Panicum scopuliferum, Panicum sellowii, Panicum seminudum, Panicum serratum, Panicum stapfianum, Panicum stipitatum, Panicum stramineum, Panicum subalbidum, Panicum sumatrense, Panicum trachyrachis, Panicum trichanthum, Panicum trichocladum, Panicum trichoides, Panicum turgidum, Panicum urvilleanum, Panicum validum, Panicum verrucosum, Panicum versicolor, Panicum virescens, Panicum virgatum, Panicum whitei*. It should be noted that there are now more than 60 known types of *Panicum* and therefore those skilled in the art will recognize that while not all are cited in this report, as mentioned above, the *Panicum* extract present in the composition, can be selected from any species belonging to the genus *Panicum* or Proso Millet.

Preferably, the extract of the genus *Panicum* used in the present invention is the extract of the species *Panicum miliaceum*, sometimes also called Millet or Proso Millet.

The extract of *Panicum miliaceum*, also known as Proso Millet, is a rich source of: (a) proteins; (b) complex B vitamins, more specifically thiamine, niacin (nicotinic acid), riboflavin, pantothenic acid and choline; and (c) amino acids, more specifically lysine, methionine, threonine and tryptophan (Duane RB; Proso Millet in North Dakota A-805 (revised), July 2007, NDSU—www.ag.ndsu.edu).

Preferably, the *Panicum miliaceum* extract of the present invention is obtained from plant seeds and may be a dry, alcoholic, hydroalcoholic or glycolic extract, and may be present in the range of about 0.01% to about 10% of the total weight of the composition. Preferably in the range of 0.1% to about 5.0% of the total weight of the composition.

The extract of *Panicum miliaceum* used in the present invention is preferably a glycolic extract, composed of 1-10% Fluid Extract, obtained from a 1:10 plant-ethanol ratio and Glycerin between 40-60%, Purified Water between 40-60%, Sodium Benzoate between 0.2-0.3% and Potassium Sorbate between 0.2-0.3%. The glycolic extract may be based on glycerol or propylene glycol.

Additionally, the composition of the present invention comprises at least one *Oryza* extract, selected from any species of the genus *Oryza*, consisting of: *Oryza abromeitiana, Oryza alta, Oryza angustifolia, Oryza aristata, Oryza australiensis, Oryza barthii, Oryza brachyantha, Oryza breviligulata, Oryza caudata, Oryza ciliata, Oryza clandestina, Oryza coarctata, Oryza collina, Oryza communissima, Oryza denudata, Oryza dewildemani, Oryza eichingeri, Oryza elongata, Oryza fatua, Oryza filiformis, Oryza formosana, Oryza glaberrima, Oryza glaberrima* subsp. *barthii, Oryza glauca, Oryza glumaepatula, Oryza glutinous, Oryza grandiglumis, Oryza granulata, Oryza guineensis, Oryza hexandra, Oryza hexandra* var. *grandiflora, Oryza indandamanica, Oryza jeyporensis, Oryza latifolia, Oryza latifolia* var. *breviaristata, Oryza latifolia* var. *grandispiculis, Oryza latifolia* var. *roschevitzi, Oryza latifolia* var. *submutica, Oryza leersioides, Oryza longiglumis, Oryza longistaminata, Oryza madagascariensis, Oryza malampuzhaensis, Oryza manilensis, Oryza marginata, Oryza meridionalis, Oryza Mexicana, Oryza meyeriana, Oryza meyeriana* var. *indandamanica, Oryza meyeriana* subsp. *tuberculata, Oryza mezii, Oryza minuta, Oryza minuta* var. *silvatica, Oryza monandra Oryza monandra* var. *grandiflora, Oryza monandra* var. *parviflora, Oryza montana, Oryza mutica, Oryza neocaledonica, Oryza nepalensis, Oryza nivara, Oryza officinalis, Oryza oryzoides, Oryza palustris, Oryza paraguayensis, Oryza parviflora, perennis Oryza, Oryza perennis* var. *breviaristata, Oryza perennis* var. *fuscella, Oryza perrieri Oryza platyphyla,* full *Oryza, Oryza praecox, Oryza prehensilis, Oryza pubescens, Oryza pumila, Oryza punctata, Oryza repens, Oryza rhizomatis, Oryza ridleyi, Oryza rubra, Oryza rubribarbis, Oryza rufipogon, Oryza sativa, Oryza sativa* var. *fatua, Oryza sativa* var. *grandiglumis, Oryza sativa* var. *latifolia, Oryza sativa* var. *paraguayensis, Oryza sativa* var. *sundensis, Oryza sativa* subsp. *fatua, Oryza sativa* subsp. *rufipogon, Oryza schlechteri, Oryza schweinfurthiana, Oryza segetalis, Oryza sorghoidea, Oryza sorghoides, Oryza stapfii, Oryza subulata, Oryza sylvestris, Oryza tisseranti, Oryza triandra, Oryza triticoides, Oryza ubanghensis.*

Preferably, the extract of the genus *Oryza* used in the present invention is the extract of the species *Oryza sativa*, obtained from plant seeds and may be a dry, alcoholic, hydroalcoholic or glycolic extract, and be in hydrolyzed or non-hydrolyzed form, and may be in the range of about 0.001% to about 5.0% of the total weight of the composition. Preferably in the range of 0.005% to about 1.0% of the total weight of the composition.

The *Oryza sativa* extract is also a rich source of protein and essential amino acids, more specifically, rich in amino acids alanine, arginine, aspartate, cysteine, glutamate, glycine, histidine, isoleucine, leucine, lysine, methionine, phenylalanine, proline, serine, threonine, tryptophan, tyrosine and valine.

The extract of *Oryza sativa* used in the present invention is preferably a glycolic hydrolyzed extract, composed of 1-10% Fluid and Hydrolyzed Extract, obtained from a 1:10 plant-ethanol ratio and Glycerin between 40-60%, purified water between 40-60%, Sodium Benzoate between 0.2-0.3% and Potassium Sorbate between 0.2-0.3%. The glycolic extract may be based on glycerol or propylene glycol.

The film forming agent in the composition of the present invention is selected from the group of water soluble film forming agents. Non-limiting examples of water soluble film forming agents may be selected from cellulose derivatives, polysaccharides (e.g. pullulan), gum arabic, or any other known water soluble film forming agent in the art, and mixtures thereof. In the present invention, the composition contains at least one film forming agent present in the range of about 0.5% to about 15% of the total weight of the composition.

According to the present invention, at least one film forming agent comprises a mixture of a polysaccharide and gum arabic. More specifically, a mixture of pullulan and gum arabic, the pullulan may be present in the range of about 7% to about 13% of the total weight of the composition, and the gum arabic may be in the range of about 0.5% to about 2% of the total weight of the composition.

In addition to the plant extracts, the film forming agents and pharmaceutically acceptable excipients, the composition, object of the present invention, may further contain optionally at least one keratin and/or biotin.

Keratin is a structural protein composed of 20 amino acids (glycine, alanine, serine, cysteine, tyrosine, aspartic acid, glutamic acid, arginine, histidine, asparagine, glutamine, proline, phenylalanine, valine, tryptamine, lysine, leucine, isoleucine, methionine and threonine) with special characteristics such as, for example, microfilaments having resistance, elasticity and water impermeability.

The keratin present in the composition, object of the present invention, can be in its hydrolyzed or non-hydrolyzed form, and in the range of about 0.1% to about 1% of the total weight of the composition. Preferably, the keratin is in its hydrolyzed form and is in the range of about 0.3% to about 0.6% of the total weight of the composition.

In the composition of the present invention biotin is present in the range of 0.001% to 0.1% of the total weight of the composition. Preferably, the biotin is present in the range of about 0.007% to about 0.02% of the total weight of the composition.

The pharmaceutically acceptable excipients included in the composition of the present invention include, but are not limited to, a viscosity agent, wetting agent, preservative, organic solvent and an aqueous vehicle.

Examples of viscosity agents include, but are not limited to, the compounds selected from the group consisting of: alginic acid, bentonite, carbomer (carbopol), methylcellulose, dimethyl sulfone, sodium alginate, gum tragacanth and mixtures thereof.

The viscosity agent may be present in the range of about 1% to about 10% of the total weight of the composition. Preferably, the viscosity agent is dimethyl sulfone and is present in the range of about 4% to about 6% of the total weight of the composition.

Examples of wetting agent include, but are not limited to, compounds selected from the group consisting of: glycerol (glycerin), propylene glycol, sorbitol, trehalose, triacetin, cyclomethicone, and mixtures thereof.

The wetting agent may be present in the composition in the range of about 0.5% to about 10% of the total weight of the composition. Preferably, the wetting agent is glycerin and is present in the range of about 1% to about 4% of the total weight of the composition.

Examples of preservative agent include but are not limited to, compounds selected from the group consisting of: phenylpropanol, bronopol, butylparaben, ethylparaben, imidazolidinyl urea, methylparaben, phenoxyethanol, sodium benzoate, potassium sorbate and mixtures thereof.

The preservative can be present in the composition of the present invention in the range of about 0.1% to 1.5% of the total weight of the composition. Preferably, the preservative agent is a mixture of sodium benzoate and potassium sorbate, and is present in the range of about 0.2% to about 0.6% of the total weight of the composition.

Examples of organic solvents include, but are not limited to, compounds selected from the group consisting of: short chain alcohols (methanol, ethanol, isopropanol, etc.), short chain ketones (acetone, methyl ethyl ketone, etc.), light hydrocarbons or a mixture of light hydrocarbons (hexane, petroleum ether, etc.), light chlorinated hydrocarbon (chloroform, methylene hydrochloride, ethylene tri chloral hydrate, etc.), and mixtures thereof.

The organic solvent may be present in the composition of the present invention in the range of about 5% to about 40% of the total weight of the composition. Preferably, the organic solvent is ethanol (ethyl alcohol) and is present in the range of about 20% to about 30% of the total weight of the composition.

An example of an aqueous vehicle is water used as the base composition in an amount sufficient for the final volume of the composition.

Another relevant aspect of the present invention relates to the method of producing the topical composition for use on the nail, said method comprising the steps of:

(a) Preparation of the colloidal phase, comprising:
  (i) In a suitable container and under slow and constant stirring, add water and mix the plant extracts, film forming agents and other compounds of the aqueous phase, such as viscosity agents, wetting agent, preservative and optionally, adding biotin and/or keratin;
  (ii) Finally, under constant agitation slowly add the organic solvent and;
(b) Maintain under moderate agitation for a period of 15 to 60 minutes;
(c) Maintain the mixture under slow agitation for a period of about 3 to 5 hours;
(d) Packaging of the composition.

EXAMPLES

It should be understood that the examples and embodiments described in detail herein illustrate the invention without, however, limiting its scope, and that various modifications or changes in light thereof will be suggestive to those skilled in the art. Such equivalent achievements should be included within the scope and reach of the accompanying claims.

Example 1: General Formulation of the Topical Composition (a) at least one plant extract of the genus *Panicum*,
(b) at least one plant extract from the genus *Oryza*,
(c) at least one film forming agent, and
(d) pharmaceutically acceptable excipients.

Optionally, the composition, object of the present invention comprises: (e) at least one keratin and (f) biotin.

Example 2: Production Method of the Compositions of Formula 1 and

The production process of the compositions of formula 1 and formula 2 (Table 1) consists of the steps described below:

TABLE 1

Compositions of formulas 1 and 2

| Feedstock | FORMULA 1 % w/w total | FORMULA 2 % w/w total |
| --- | --- | --- |
| Hydrolyzed glycolic extract of *Oryza sativa* | 0.500 | 0.010 |
| Glycolic extract of *Panicum miliaceum* | 5.000 | 0.100 |
| Biotin | 0.010 | 0.010 |
| Hydrokeratin | 0.500 | 0.500 |
| Dimethyl sulfone | 5.000 | 5.000 |
| Pullulan | 8.000 | 8.000 |
| Gum arabica | 1.000 | 1.000 |
| Glycerin | 2.680 | 2.680 |
| Sodium benzoate | 0.186 | 0.200 |
| Potassium sorbate | 0.186 | 0.200 |
| Ethyl alchohol | 25.000 | 25.000 |
| Water | qsp 100 (51.938) | qsp 100 (57.300) |

(i) Preparation of the Colloidal Solution
  a) In an appropriate container under slow and constant stirring, add the total water calculated to qsp of the final volume (100%) and dissolve the biotin and preservatives, sodium benzoate and potassium sorbate;
  b) After dissolution, add the pullulan to the mixture under slow stirring until complete dissolution.
  c) In sequence add the GUM ARABIC under slow stirring until complete dissolution;
  d) Add the dimethyl sulfone to the mixture under slow stirring until complete dissolution;
  e) Add the hydrokeratin, the extract of *Panicum miliaceum*, the extract of *Oryza sativa* and glycerin slowly to the mixture under stirring until complete dissolution;
  f) Finally, add the ethanol slowly to the mixture and stir until complete homogenization of the mixture;
  g) If necessary, adjust the final volume with water (qsp);
  h) Maintain the mixture under moderate agitation for a period of about 40 to 60 minutes until complete homogenization and uniform phase formation; and
  i) After complete homogenization, maintain the mixture under slow agitation for a period of approximately 4 hours.
(ii) Packaging of the Composition.

The compositions of formula 1 and 2, obtained according to the process described above, are indicated for topical use on the nail, and present a clear and homogeneous appearance and a slightly yellowish color. The compositions of formula 1 and 2, after applied to the nail, were capable of forming a transparent and non-glossy film and strongly adhered to the nail, and did not cause irritation to the adjacent skin or the periungueal bed.

Example 3: Efficacy Study of the Composition of Formula 1

A clinical study with the composition, object of the present invention, was performed in women and/or men with nail changes, such as those described in the syndrome of fragile nails (onychoschizia, onychorexis, etc.) resulting from nail diseases or exogenous causes such as, for example, chemical agents or trauma.

In the study was used the composition of formula 1, described in example 2 as well as compositions with variations in components (table 2). These compositions were applied to volunteers to evaluate the effectiveness of the complete composition, and the isolated active ingredients or in combination with and without the presence of film forming agents, during a predefined period of 28 days.

TABLE 2

Altered formulas used in the study

| Ingredient | Group 1 % | 2 % | 3 % | 4 % | 5 % |
|---|---|---|---|---|---|
| Gum arabica | 1 | 1 | non | non | non |
| Ethyl alcohol | 25 | 25 | 25 | 25 | 25 |
| Aqua qsp | qsp | qsp | qsp | qsp | qsp |
| Hydrolyzed glycolic extract of *Oryza sativa* | non | 0.5 | 0.5 | non | 0.5 |
| Glycolic extract of *Panicum miliaceum* | non | 5 | non | 5 | 5 |
| Glycerin | 2.68 | 2.68 | 2.68 | 2.68 | 2.68 |
| Potassium sorbate and sodium benzoate | 0.4 | 0.4 | 0.4 | 0.4 | 0.4 |
| Pullulan | 8 | 8 | non | non | non |
| Total | 100 | 100 | 100 | 100 | 100 |

Legend:
non-indicates absence of the ingredient

Voluntary recruitment and execution stage of the trial was performed for the study.

57 (fifty-seven) female participants were selected, according to the criteria of inclusion and non-inclusion listed in the table below.

TABLE 3

Inclusion and exclusion criteria

| Inclusion Criteria | Exclusion Criteria |
|---|---|
| 1. Participants not menopausal women; | 1. Pregnancy or risk pregnancy; |
| 2. Age 18-45 years; | 2. Lactation; |
| 3. Complaint weak nails with peeling without cause and/or degree of laminar separation and/or mild or moderate transverse partition; | 3. Degree of laminar separation and stern transverse partition; |
| | 4. Signs of specific diseases in fingernails (onychomycosis, psoriasis, etc.); |
| 4. Agreement not to use nail polish or remover or other any products on site to be studied (nails); | 5. History of nutritional deficiencies (anemia, iron deficiency or vitamin A deficiency, among others) or hormonal changes; |
| | 6. History of endocrine disorders (hypo- or hyperthyroidism, diabetes); |
| 5. Agreement to abide by the procedures and requirements of the test and attend the Institute at (s) day (s) and time (s) set (s) for evaluations; | 7. Deficiency disorders; |
| | 8. Use of any continuous medication; |
| | 9. Introduction of restrictive diet in the last 03 months; |
| | 10. Other conditions considered by the medical evaluator as reasonable for disqualification from participation in the study. |

The age of the volunteers included in the study was from 18 to 45 with a mean age of 33 years. Of the 57 volunteers screened, 51 (fifty-one) completed the study, and none presented a confirmed or reported reaction in the region evaluated during the study.

Samples for the study are standardized with a label identifying only: the type of product, code, validity, sample lot, and identification of the group as listed below:
P1=FF—Group 1
P2=FF+PA+OS—Group 2
P3=OS—Group 3
P4=PA—Group 4
P5=PA+OS—Group 5
P6=Formula 1 of Example 2—Group 6
Legend: FF=film former; PA=glycolic extract of *Panicum miliaceum*; OS=glycolic extract of *Oryza Sativa*.

The volunteers were instructed to apply the sample evenly on the nails and cuticles every day with the aid of the brush and always to reapply after the washing of hands. For best results, avoid the use of nail polish during the use of the product.

During the first visit, called D0, the volunteers are evaluated by a doctor who checks the criteria for inclusion and non-inclusion of the study and evaluates some signs that characterize weak nails such as delamination, flaking, transverse and longitudinal separation, the presence of ridges and grooves, nail thickening or thinning and hydration.

Following the clinical evaluation, the eligible participants were referred to the instrumental efficiency area to perform the photographic record of the nails.

At the end of the photographic record, the participants were kept in the area and remained in air conditioning for a period of 20 minutes under controlled environmental conditions (Temperature: T=20±2° C. and Relative Humidity: RH=50±5%).

The study participants were randomly divided into six groups. After randomization, the participants were discharged and received the samples relative to their group, which would be used throughout the study, along with a copy of the form containing all information pertinent to the use of the product. In addition, they were informed of the dates of return to the Research Center for the next visit.

Participants were instructed to return after 07 (D7) and 28 (D28) days of product use for new evaluations. During the intermediate visit (D7) were reinforced the guidelines for non-use nail polish or removers or any other products at the site to be studied (nails).

On the visits of D7 and D28 the participants returned to the Research Center for a new clinical evaluation, instrumental and photographic record, in the same way as the initial visit. At the end of the evaluations, the participants answered a subjective questionnaire and were dismissed, and during the D7 visit, the volunteers were asked to return after 28 days of use of the product. The study was completed after the 28-day visit.

Through the clinical evaluation performed on return visits (visual analysis), it can be concluded that:

Group I—Improvement was observed between the experimental time D28 in relation to the initial time (D0) for the parameters: delamination, transverse separation, spontaneous breaking and cuticle appearance.

Group II—Significant improvement was observed between the experimental time D28 in relation to the initial time (D0) for the parameters: delamination, spontaneous breaking and aspect of the cuticle.

Group III—No significant improvement was observed in any of the parameters.

Group IV—Significant improvement was observed between the experimental time D28 in relation to the initial time (D0) for the parameters: delamination and spontaneous breaking.
Group V—No significant improvement was observed in any of the parameters.
Group VI—Significant improvement was observed between experimental periods D7 and D28 at the initial time (D0) for the parameters: delamination, peeling, transverse partition longitudinal separation, thickening/thinning of the nail and spontaneous nail breakage. For the aspect parameter of the cuticles there was significant improvement in D7.

Instrumental Evaluation of Degree of Nail Desquamation

For the instrumental evaluation of peeling of the nails after the capture of photographic records at days (D0, D7 and D28 days), the chosen nail image was analyzed using the Image Pro software: the chosen nail for the analysis was that which had the highest number of scales in order to show the action of the product.

From the image analysis, the degree of peeling was quantified and compared between the experimental period, indicating improvement (decreased frequency of red dots) or worsening (increase) after use of the product. The results are shown in Table 4 and in FIG. 1.

The D0 reading (initial study visit) was considered as 100% desquamation and the results obtained in visits D7 and D28 were evaluated if there was a reduction or an increase of nail desquamation. The results are expressed as percentages, with results below 100% demonstrating an improvement in nail desquamation and results above 100% demonstrating a worsening of nail desquamation.

TABLE 4

Desquamation of nails by time of use of the product (%)

| Days | GROUP 1 FF | GROUP 2 FF + PA + OS | GROUP 3 OS | GROUP 4 PA | GROUP 5 PA + OS | GROUP 6 Formula 1 |
|---|---|---|---|---|---|---|
| D 0 | 100.000 | 100.000 | 100.000 | 100.000 | 100.000 | 100.000 |
| D 7 | 92.045 | 78.869 | 98.624 | 50.391 | 45.316 | 48.122 |
| D 28 | 80.742 | 62.523 | 86.314 | 68.200 | 50.380 | 26.481 |

A reduction of desquamation of the nails after 7 (D7) and 28 days (D28) of use of the products in the tested groups was observed.

Group V showed improvement in desquamation of the nails when compared with groups I, II, III and IV after 07 (D7) and 28 days (D28) using the product.

Group VI presented a significant decrease in desquamation of the nails after 07 (D7) and 28 days (D28) using the product with the results for this group being far superior to the others.

The invention described herein is not limited to this embodiment, and those skilled in the art will realize that any particular feature introduced herein is to be understood only as something that has been described for ease of understanding and has been performed without departing from the described inventive concept. The limiting features of the object of the present invention are related to the claims which form part of the present report.

The invention claimed is:

1. Dermocosmetic composition for topical use, comprising:
   (a) at least one plant extract of the genus *Panicum*,
   (b) at least one plant extract from the genus *Oryza*,
   (c) at least one film forming agent, and
   (d) pharmaceutically acceptable excipients;
   wherein the composition is effective for the treatment of nail disorders.

2. Dermocosmetic composition according to claim 1, wherein the composition further comprises:
   (e) at least one keratin; and/or
   (f) biotin.

3. Dermocosmetic composition according to claim 1, wherein the composition is in the form of a pharmaceutical gel, nail polish, lotion, solution or suspension.

4. Dermocosmetic composition according to claim 1, wherein the extract of the genus *Panicum* is the extract of *Panicum miliaceum*.

5. Dermocosmetic composition according to claim 1, wherein the extract is dried, alcoholic, hydroalcoholic or glycolic.

6. Dermocosmetic composition according to claim 1, wherein the *Panicum* extract is obtained from plant seeds and is present in the range of about 0.01% to about 10.0% by total weight of the composition.

7. Dermocosmetic composition according to claim 6, wherein the *Panicum* extract is present in the range of about 0.1% to about 5.0% of the total weight of the composition.

8. Dermocosmetic composition according to claim 5, wherein the *Panicum* extract is a glycolic extract.

9. Dermocosmetic composition according to claim 1, wherein the extract of the genus *Oryza* is an extract of *Oryza sativa*.

10. Dermocosmetic composition according to claim 9, wherein the extract is dried, alcoholic, hydroalcoholic or glycolic, either hydrolyzed or non-hydrolyzed.

11. Dermocosmetic composition according to claim 1, wherein the extract is obtained from plant seeds and is in the range of about 0.001% to about 5.0% of the total weight of the composition.

12. Dermocosmetic composition according to claim 11, wherein the extract of *Oryza* is present in the range of about 0.005% to about 1.0% of the total weight of the composition.

13. Dermocosmetic composition according to claim 10, wherein the extract of *Oryza* is a hydrolyzed glycolic extract.

14. Dermocosmetic composition according to claim 1, wherein the film forming agent is selected from the group of water soluble film forming agents consisting of cellulose derivatives, polysaccharides, gum arabic, or any other film forming agent soluble in water and mixtures thereof.

15. Dermocosmetic composition according to claim 14, wherein the film forming agent comprises a mixture of gum arabic and polysaccharides, and is present in the range of about 0.5% to about 15% of the total weight of the composition.

16. Dermocosmetic composition according to claim 15, wherein the polysaccharides is a pullulan and in the range of about 7% to about 13% of the total weight of the composition and gum arabic in the range of about 0.5% to about 2% of the total weight of the composition.

17. Dermocosmetic composition according to claim 2, wherein the keratin is in its hydrolyzed or non-hydrolyzed form, and is present in the range of about 0.1% to about 1% of the total weight of the composition and biotin is present in the range 0.001% to 0.1% of the total weight of the composition.

18. Dermocosmetic composition according to claim 17, wherein the keratin is in the form of hydrolysate and is present in the range of about 0.3% to about 0.6% of the total weight of the composition and biotin is present in the range of about 0.007% to about 0.02% of the total weight of the composition.

19. Dermocosmetic composition according to claim 1, wherein the pharmaceutically acceptable excipients include, but are not limited to, viscosity agent, wetting agent, preservative, organic solvent and an aqueous vehicle.

20. Dermocosmetic composition according to claim 19, wherein the viscosity agents are selected from the group consisting of: alginic acid, bentonite, carbomer (carbopol), methylcellulose, dimethyl sulfone, sodium alginate, tragacanth and mixtures thereof and are present in the range of about 1% to about 10% of the total weight of the composition.

21. Dermocosmetic composition according to claim 20, wherein the viscosity agent is dimethyl sulfone and is present in the range of about 4% to about 6% of the total weight of the composition.

22. Dermocosmetic composition according to claim 19, wherein the wetting agent is glycerin and is present in the range of about 1% to about 4% of the total weight of the composition.

23. Dermocosmetic composition according to claim 19, wherein the preservative agent is selected from the group consisting of: phenyl propanol, bronopol, butylparaben, ethylparaben, imidazolidinyl urea, methylparaben, phenoxyethanol, sodium benzoate, potassium sorbate and mixtures thereof and is in range from about 0.1% to 1.5% of the total weight of the composition.

24. Dermocosmetic composition according to claim 23, wherein the preservative agent is a mixture of sodium benzoate and potassium sorbate and is present in the range of about 0.2% to about 0.6% of the total weight of the composition.

25. Dermocosmetic composition according to claim 19, wherein the organic solvent is ethanol (ethyl alcohol) and is present in the range of about 20% to about 30% of the total weight of the composition.

26. Dermocosmetic composition according to claim 19, wherein the aqueous vehicle is water in sufficient quantity for the final volume of the composition.

27. Dermocosmetic composition according to claim 1, wherein it acts on the nail protection, nail strengthening and recovery of nail disorders.

* * * * *